(12) United States Patent
Yodfat et al.

(10) Patent No.: US 9,919,105 B2
(45) Date of Patent: Mar. 20, 2018

(54) DEVICES, SYSTEMS AND METHODS FOR QUANTIFYING BOLUS DOSES ACCORDING TO USER PARAMETERS

(75) Inventors: Ofer Yodfat, Modi'in (IL); Gali Shapira, Haifa (IL); Iddo M. Gescheit, Tel-Aviv (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1121 days.

(21) Appl. No.: 13/496,716

(22) PCT Filed: Sep. 16, 2010

(86) PCT No.: PCT/IL2010/000757
§ 371 (c)(1),
(2), (4) Date: Jun. 26, 2012

(87) PCT Pub. No.: WO2011/033509
PCT Pub. Date: Mar. 24, 2011

(65) Prior Publication Data
US 2012/0283694 A1    Nov. 8, 2012

Related U.S. Application Data

(60) Provisional application No. 61/243,860, filed on Sep. 18, 2009.

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61B 5/4839* (2013.01); *G06F 19/3468* (2013.01)

(58) Field of Classification Search
CPC ........... A61M 2230/201; A61M 5/1723; G06F 19/3468; G06F 19/3456; A61B 5/14532; A61B 5/4839
(Continued)

(56) References Cited

U.S. PATENT DOCUMENTS 6,936,029 B2    8/2005   Mann et al.
2005/0187749 A1    8/2005   Singley
(Continued)

FOREIGN PATENT DOCUMENTS

WO    WO 2008/078319 A1    7/2008
WO    WO-2009048462 A1    4/2009
(Continued)

OTHER PUBLICATIONS

DCCT Trial, N. Engl J. Med 1993; 329: 977-986.
(Continued)

*Primary Examiner* — Imani Hayman
(74) *Attorney, Agent, or Firm* — Dinsmore & Shohl LLP

(57) ABSTRACT

Devices, systems and methods for determining a recommended bolus dose of therapeutic fluid to be delivered to the body are disclosed. Such a recommended bolus dose may be provided by establishing an initial bolus dose for a user based on one or more first parameters relating to the user and adjusting (e.g., increasing or decreasing) this initial bolus dose amount based on one or more second user parameters by multiplying the initial bolus dose by one or more multiplier values that correlate to at least one of the second parameters and/or by adding or subtracting an absolute value of at least one of the second parameters from the initial bolus dose amount.

22 Claims, 8 Drawing Sheets

(51) Int. Cl.
*A61B 5/00* (2006.01)
*G06F 19/00* (2018.01)

(58) Field of Classification Search
USPC ..... 604/31, 65–67, 347, 365, 500, 503–504, 604/890.1–892.1
See application file for complete search history.

(56) References Cited

U.S. PATENT DOCUMENTS

| | | | |
|---|---|---|---|
| 2005/0192494 A1* | 9/2005 | Ginsberg | G06F 19/3456 600/365 |
| 2005/0272640 A1 | 12/2005 | Doyle et al. | |
| 2006/0173406 A1 | 8/2006 | Hayes et al. | |
| 2007/0106218 A1 | 5/2007 | Yodfat et al. | |
| 2007/0191702 A1 | 8/2007 | Yodfat et al. | |
| 2008/0172031 A1* | 7/2008 | Blomquist | 604/500 |
| 2008/0183060 A1 | 7/2008 | Steil et al. | |
| 2008/0214916 A1 | 9/2008 | Yodfat et al. | |
| 2008/0220403 A1 | 9/2008 | Marling et al. | |
| 2008/0228056 A1 | 9/2008 | Blomquist et al. | |
| 2008/0234663 A1 | 9/2008 | Yodfat et al. | |
| 2009/0018406 A1 | 1/2009 | Yodfat et al. | |
| 2009/0054750 A1 | 2/2009 | Jennewine | |
| 2010/0262434 A1* | 10/2010 | Shaya | 705/3 |
| 2010/0292634 A1* | 11/2010 | Kircher, Jr. | A61B 5/14532 604/66 |

FOREIGN PATENT DOCUMENTS

| | | |
|---|---|---|
| WO | WO 2009/066288 A1 | 5/2009 |
| WO | WO 2009/125398 A2 | 10/2009 |
| WO | WO 2009/133558 A2 | 11/2009 |

OTHER PUBLICATIONS

UKPDS Trial, Lancet 1998; 352: 837-853.
BMJ 1998; 317. (7160): 703-13.
EDIC Trial, N Engl J Med 2005; 353, (25): 2643-53.
Journal of Diabetes Science and Technology, 2007 vol. I (5), 780-793.
International Search Report issued on parent PCT application No. PCT/IL2010/00757, dated Jan. 11, 2011.

* cited by examiner

DEVICES, SYSTEMS AND METHODS FOR QUANTIFYING BOLUS DOSES ACCORDING TO USER PARAMETERS

CROSS-REFERENCE TO RELATED APPLICATIONS

The present application is a 35 U.S.C. § 371 national stage entry of PCT/IL2010/000757, which has an international filing date of Sep. 16, 2010 and claims priority to U.S. Provisional Application No. 61/243,860, filed on Sep. 18, 2009 and entitled "Device and Method for Quantification of Insulin Bolus Dosages," the disclosures of which are incorporated herein by reference in their entireties.

FIELD

Devices, systems and methods for sustained medical infusion of therapeutic fluids (e.g., insulin) are described herein. Some embodiments specifically relate to portable infusion devices and methods for quantifying bolus doses. Some embodiments more specifically relate to insulin dispensing devices, systems and methods for recommending a new bolus dose by adjusting an original bolus dose by a certain magnitude according to one or more user parameters.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically-raised blood glucose concentration (hyperglycemia) due to a relative or absolute lack of the pancreatic hormone, insulin. Within the healthy pancreas, beta cells, located in the islets of Langerhans, continuously produce and secrete insulin according to blood glucose concentrations ("BG levels"), maintaining near-constant glucose levels in the body.

Much of the burden of the disease to the user and to health care resources is due to the long-term tissue complications, which affect both small blood vessels (microangiopathy, causing eye, kidney and nerve damage) and large blood vessels (causing accelerated atherosclerosis, with increased rates of coronary heart disease, peripheral vascular disease and stroke). The Diabetes Control and Complications Trial ("DCCT") demonstrated that development and progression of the chronic complications of diabetes are greatly related to the degree of altered glycemia as quantified by determinations of glycohemoglobin (HbA1c). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining euglycemia by frequent glucose measurements and adjustment of insulin delivery accordingly is of utmost importance.

Conventional insulin pumps deliver rapid-acting insulin 24 hours a day through a catheter placed under the skin. The insulin total daily dose ("TDD") is typically divided into basal and bolus doses. Basal insulin is delivered continuously over 24 hours and is intended to keep the BG levels within acceptable ranges between meal times and overnight.

Bolus doses may be delivered during episodes of high BG levels (e.g., a "correction bolus" or "CB") or, when delivered before, during or after meals to counteract carbohydrate loads (e.g., a "meal bolus" or "MB"). Conventional parameters used for determining bolus doses include without limitation at least one of the following:

- the amount of carbohydrates consumed or to be consumed ("TC");
- the carbohydrate-to-insulin ratio ("CIR")—the amount of carbohydrates balanced by one unit of insulin measured in grams per unit of insulin. A high or low CIR value indicates that a high or low amount of carbohydrates can be "covered" by one unit of insulin, respectively;
- insulin sensitivity ("IS")—the amount of blood glucose lowered by one unit of insulin measured in milligrams per deciliter (mg/dL) per unit of insulin;
- current blood glucose levels ("CBG") measured in mg/dL;
- target blood glucose levels ("TBG")—a desired blood glucose level measured in mg/dL; and/or
- residual insulin ("RI")—the amount of stored active insulin remaining in the body of a patient after delivery of a bolus dose (also known as bolus-on-board or "BOB").

Additional parameters (e.g., glycemic index) can be also used, and different units can be used, for example "mmol" instead of "mg/dL".

Conventional insulin pumps may provide bolus dose recommendations based on one or more of the above-listed parameters. For example, an MB dose may be calculated by dividing the amount of carbohydrates by the CIR. In U.S. Pat. No. 6,936,029 to Mann et al., a recommended bolus dose is calculated based on all of the above-listed parameters as follows:

$$\underbrace{(TC/CIR)}_{\text{"Food Estimate"}} + \underbrace{[(CBG-TBG)/IS]}_{\text{"Correction Estimate"}} -$$

$$RI = \text{Recommended Bolus Dose}$$

In a non-meal CB dose, the above formula may be simplified as follows because the TC and RI are not considered:

Recommended Bolus Dose=(CBG−TBG)/IS

Some of the above-mentioned parameters are also considered in the bolus dose recommendation feature described in U.S. Patent Application Publication No. US2008/0234663 to Yodfat et al. and International Publication No. WO 2009/133558, to Yodfat et al., the disclosures of which are incorporated herein by reference in their entireties. These publications describe this feature (hereinafter "bolus selector feature") as comprising sets of grids of ranges of carbohydrate amounts and blood glucose concentrations, wherein each grid may correspond to a different combination of IS, CIR and/or TBG, according to some embodiments. The publications also note that additional grids may correspond to selected bolus doses and RI values. The final recommended bolus dose, according to some embodiments, may be related to a value that is substantially equivalent to the selected bolus dose minus the RI.

Currently-available continuous glucose monitors ("CGMs") provide continuous "real-time" BG level readings, including the direction and rate of change of BG level (i.e., "BG trends"). This feature assesses the BG trend and enables diabetics to determine (manually) a bolus dose that roughly taken into consideration the BG trend, to improve their glycemic control by responding quickly to rising and/or falling BG levels. The BG trends may, for example, be displayed graphically as trend arrows according to BG level change rates as follows:

↑=glucose rising quickly: >2 (mg/dL)/min=
↗=glucose going up: 1 to 2 (mg/dL)/min=
→=fairly stable glucose: −1 to 1 (mg/dL)/min
↘=glucose going down: −1 to −2 (mg/dL)/min
↓=glucose falling quickly: <−2 (mg/dL)/min The abovementioned general formula for determining a recommended bolus dose does not take into account numerous rapidly-changing parameters or physiological conditions (such as without limitation BG trends, physical activity levels (e.g., exercise or sedentary state), illness (e.g., high temperature) or emotional stress) that may influence or otherwise substantially modify the recommended bolus dose determination. In addition, rapidly-changing blood-related parameters, including without limitation, BG levels, ketones, PH levels or blood gases, may also influence or otherwise substantially modify the recommended bolus dose. For example, the same 5 U of insulin may have a substantially different effect on a person when he or she is exercising as compared to when that person is sleeping.

While BG level is one of the most important rapidly-changeable parameters, the abovementioned formula only considers the current BG level (i.e., a discrete value) and not BG trends and other user-specific parameters, including those identified above. For example, if a high discrete BG level is measured, the formula recommends delivering a large bolus dose to bring the user's BG levels back to TBG. In situations where consecutive BG level measurements are consistently high (i.e., BG level is substantially constant), such a recommended bolus dose may be appropriate. However, if the high-measured BG is increasing or decreasing, a relatively higher or lower bolus dose may be more properly recommended.

For example, using the following parameters, the abovementioned formula provides a bolus dose of 2 U:

IS=50 mg/dL per unit of insulin
TBG=100 mg/dL
CBG=200 mg/dL
CGM trend=rising>2 mg/dL per min,
Bolus Dose=(CBG−TBG)/IS=(200 mg/dL−100 mg/dL)/50 (mg/dL)/U=2 U.

In this case, however, the recommendation may be too low because the BG level will be 260 mg/dL within 30 minutes and 320 mg/dL within an hour.

Thus, there is a need for a bolus dose recommendation system and methodology that considers additional user parameters that affect the recommended bolus dose determination. One such parameter is the trend of the BG level.

SUMMARY

Devices, systems and methods for delivering therapeutic fluid (e.g., insulin) and determining a recommended amount based on one or more user parameters are provided herein. The mechanism or feature for determining a recommended bolus dose amount based on one or more user parameters (e.g., variable or conditions) may be referred to as the "bolus advisor." To this end, the bolus advisor may be configured to operate within or in conjunction with a fluid dispensing system. In some embodiments, the bolus advisor may be implemented in a fluid dispensing unit and, in particular, in a portable therapeutic fluid infusion pump.

Some embodiments of the present disclosure may be directed to a method for determining a bolus dose of therapeutic fluid to be delivered to the body of a user. In some embodiments, the method may include receiving a CBG of the user, receiving a BG trend of the user, receiving one or more first additional parameters relating to the user and/or determining a bolus dose based on at least one of the CBG, the BG trend and the one or more first additional parameters relating to the user, such that delivering the bolus dose to the user may compensate for a change in a BG level of the user.

According to some embodiments, the one or more first additional parameters relating to the user may be selected from a group consisting of IS, CIR, TBG, TC and RI. In some embodiments the one or more first additional parameters relating to the user may be further selected from a group consisting of GI, fat content of a meal and fiber content of the meal.

The CBG may be measured using a CGM and/or the BG trend may be received from a CGM.

Some method embodiments may involve at least one of the one or more first additional parameters relating to the user, the CBG and the BG trend being received via a user interface.

Some embodiments may also include notifying the user, for example, regarding the bolus dose and/or delivering the therapeutic fluid according to the bolus dose.

In some embodiments, the therapeutic fluid may be insulin.

Some embodiments may also include delivering the therapeutic fluid according to the bolus dose.

Some method embodiments may also include determining an initial bolus dose for the user based on at least one of the one or more first additional parameters relating to the user and the CBG and determining the bolus dose based on the initial bolus dose and the BG trend. The bolus dose may be less than the initial bolus dose if the BG trend is decreasing, greater than the initial bolus dose if the BG trend is increasing and/or substantially equal the initial bolus dose if the BG level of the user is substantially constant.

In some embodiments increasing may include moderate increasing (e.g., going up) or steep increasing (e.g., quickly rising). Decreasing may include moderate decreasing (e.g., going down) or steep decreasing (e.g., falling quickly).

In some embodiments, delivering the bolus dose to the user may compensate for a rate of the change in the BG level of the user.

In some embodiments, methods for determining a bolus dose of therapeutic fluid to be delivered to the body of a user may include determining an initial bolus dose based on at least one of the one or more first additional parameters relating to the user and the CBG and/or determining the bolus dose based on the initial bolus dose and one or more multiplier values. Some embodiments may involve determining the bolus dose by multiplying the initial bolus dose by the one or more multiplier values.

In some method embodiments, the one or more multiplier values may be greater than 1 when the BG trend is increasing, less than 1 when the BG trend is decreasing and/or substantially equal to 1 when the BG level is substantially constant.

Some method embodiments may further include retrieving, from a memory, one or more multiplier values correlating to the BG trend.

The one or more multiplier values may be determined based on a mathematical function that correlates the BG trend with the one or more multiplier values, according to some embodiments.

Embodiments of the methods may include any of the features described in the present disclosure, including without limitation any one or more of the methods and systems, as well as any one or more of the above and/or following features.

In some related embodiments, the methods may include averaging a plurality of the one or more multiplier values, wherein at least one of the one or more multiplier values correlates to the BG trend and determining the bolus dose includes determining the bolus dose based on the initial bolus dose and the average of the plurality of the one or more multiplier values.

Some method embodiments for determining the bolus dose may also include determining an initial bolus dose based on at least one of the one or more first additional parameters relating to the user and the CBG and determining a bolus dose based on the initial bolus dose and one or more absolute values. In some related embodiments, determining the bolus dose may include adding or subtracting the one or more absolute values to or from the initial bolus dose.

In some method embodiments, the one or more absolute values may be added when the BG trend is increasing, subtracted when the BG trend is decreasing and/or substantially equal to 0 when the BG level is substantially constant.

In some embodiments, methods may include retrieving, from a memory, one or more absolute values corresponding to the BG trend.

The one or more absolute values may also be determined based on a mathematical function that correlates the BG trend with the one or more absolute values, according to some embodiments.

Embodiments of the methods may include any of the features described in the present disclosure, including without limitation any one or more of the methods and systems, as well as any one or more of the above and/or following features.

Some method embodiments for determining a bolus dose of therapeutic fluid to be delivered to the body of a user may further be directed to receiving one or more second additional parameters relating to the user, where the one or more second additional parameters may be selected from the group consisting of physical activity level, emotional stress level, blood ketones level and/or trend, blood pH level and/or trend, presence of an illness and/or menstruation and body temperature. Such method embodiments may also include determining a bolus dose that compensates for a change in the BG level of the user and/or the one or more second additional parameters relating to the user.

Some embodiments may also include adjusting a timing and/or duration associated with the bolus dose based on at least the BG trend. In some embodiments determining the bolus dose may be based on at least one of the one or more first additional parameters relating to the user and the CBG. Adjusting the timing and/or duration associated with the bolus dose may be based on at least the BG trend.

Some method embodiments may be directed to determining a recommended bolus dose of therapeutic fluid for delivery to the body and may include determining an initial bolus dose for a user based on one or more first parameters relating to the user, inputting one or more second parameters relating to the user, correlating a multiplier value with at least one of the one or more second parameters and/or deriving a recommended bolus dose by multiplying the initial bolus dose by the multiplier value of at least one of the one or more second parameters. In some embodiments, determining a recommended bolus dose may include determining an initial bolus dose for a user based on one or more first parameters relating to the user, inputting one or more second parameters relating to the user, correlating a multiplier value with at least one of the one or more second parameters and deriving a recommended bolus dose by multiplying the initial bolus dose by the multiplier value of at least one of the one or more second parameters.

In some embodiments, methods for recommending a bolus dose in accordance with a BG trend for use with an insulin delivery device may include providing a non-BG trend dependent bolus dose, receiving a BG trend, correlating the BG trend with one or more multiplier values and/or absolute values, multiplying the multiplier value with the non-BG trend dependent bolus dose and/or adding or subtracting the absolute value from the non-BG trend dependent bolus dose to obtain the BG trend dependent bolus dose and recommending an appropriate insulin dosage in accordance with the BG trend.

System embodiments of the present disclosure may be directed to a fluid delivery system for delivering a recommended bolus dose of therapeutic fluid into the body and having a dispensing unit and, in some embodiments, a remote control unit.

In some embodiments, the system may involve delivering a bolus dose of therapeutic fluid into the body of a user and includes a pump for delivering therapeutic fluid into the body and at least one processor including instructions operating thereon. The processor may be configured, depending on the embodiment, to receive a CBG of the user, a BG trend of the user and/or one or more first additional parameters relating to the user. The processor may also determine a bolus dose based on at least one of the CBG, the BG trend and the one or more first additional parameters relating to the user, such that delivering the bolus dose to the user compensates for a change in a BG level of the user.

According to some embodiments, the one or more first additional parameters relating to the user may be selected from a group consisting of IS, CIR, TBG, TC and RI. In some embodiments, the one or more first additional parameters relating to the user may be further selected from a group consisting of GI, fat content of a meal and fiber content of the meal.

In some embodiments, the processor may also include instructions configured to deliver the therapeutic fluid according to the bolus dose. In some embodiments, the recommended bolus dose may be delivered to the user upon confirmation received via a user interface.

In some embodiments, a CGM may be used for measuring the CBG and/or transmitting the BG trend.

Some embodiments may include notification means for notifying the user, for example, regarding the bolus dose.

In some system embodiments, the therapeutic fluid may be insulin.

Some system embodiments may further include a user interface for inputting at least one of the one or more first additional parameters relating to the user, the CBG and the BG trend.

The system may include a processor having instructions configured to determine an initial bolus dose based on at least one of the one or more first additional parameters relating to the user and the CBG and/or determine the bolus dose based on the initial bolus dose and one or more multiplier values. The processor in some embodiments may include instructions configured to multiply the initial bolus dose by the one or more multiplier values. In some system embodiments the processor may determine the bolus dose based on the result of the multiplication.

In some system embodiments for delivering a recommended bolus dose of therapeutic fluid into the body, the one or more multiplier values may be greater than 1 when the BG trend is increasing, less than 1 when the BG trend is decreasing and/or substantially equal to 1 when the BG level of the user is substantially constant.

In some embodiments increasing may include moderate increasing (e.g., going up) or steep increasing (e.g., quickly rising). Decreasing may include moderate decreasing (e.g., going down) or steep decreasing (e.g., falling quickly).

In some embodiments, the system may further include a memory storing the one or more multiplier values correlating to the BG trend. In some related embodiments, the processor may have instructions configured to retrieve from the memory the one or more multiplier values.

In some embodiments, the one or more multiplier values may be determined based on a mathematical function that correlates the BG trend with the one or more multiplier values.

In some embodiments, the processor may include instructions configured to average a plurality of the one or more multiplier values, with at least one of the one or multiplier values correlating to the BG trend. The processor may also determine the bolus dose based on the initial bolus dose and the averaged multiplier values.

Embodiments of the systems may include any of the features described in the present disclosure, including any of the features described above in relation to the methods as well as any one or more of the above and/or following features.

In some system embodiments, the processor may include instructions configured to determine an initial bolus dose of therapeutic fluid based on at least one of the one or more first additional parameters relating to the user and the CBG. The processor may also determine a bolus dose based on the initial bolus dose and one or more absolute values. The processor may include instructions configured to add or subtract the one or more absolute values to or from the initial bolus dose.

In some embodiments, one or more absolute values may be added when the BG trend is increasing, subtracted when the BG trend is decreasing and/or substantially equal to 0 when the BG level of the user is substantially constant.

In some embodiments, the system may further include a memory storing the one or more absolute values correlating to the BG trend. In some related embodiments, the processor may have instructions configured to retrieve from the memory the one or more absolute values.

In some embodiments, the one or more absolute values may be determined based on a mathematical function that correlates the BG trend with the one or more absolute values.

Embodiments of the systems may include any of the features described in the present disclosure, including any of the features described above in relation to the methods as well as any one or more of the above and/or following features.

In some system embodiments, the processor may include instructions configured to receive one or more second additional parameters relating to the user, the one or more second additional parameters being selected from the group consisting of physical activity level, emotional stress level, blood ketones level and/or trend, blood pH level and/or trend, presence of an illness and/or menstruation and body temperature. The processor may also determine a bolus dose that compensates for a change in the BG levels of the user and/or the one or more second additional parameters.

In some system embodiments, the processor may include instructions configured to adjust a timing and/or duration associated with the bolus dose based on at least the BG trend. In some embodiments determining the bolus dose may be based on at least one of the one or more first additional parameters relating to the user and the CBG. Adjusting the timing and/or duration associated with the bolus dose may be based on at least the BG trend.

The processor may also, according to some embodiments, have instructions configured to determine an initial bolus dose for the user based on at least one of the one or more first additional parameters relating to the user and the CBG and determine the bolus dose based on the initial bolus dose and the BG trend. In some embodiments, the bolus dose may be less than the initial bolus dose if the BG trend is decreasing, greater than the initial bolus dose if the BG trend is increasing and substantially equal to the initial bolus dose if the BG level of the user is substantially constant.

Some system embodiments may also involve delivering the bolus dose to the user to compensate for a rate of the change in the BG level of the user.

Some system embodiments may include a display for presenting the recommended bolus dose of the therapeutic fluid to the user. The display may be located on the dispensing unit and/or on a remote control.

Some system embodiments may include a memory for storing one or more of: the one or more parameters relating to the user, a database of the BG trends and corresponding multiplier values, mathematical function that correlates the BG trends and multiplier values, a database of the BG trends and corresponding absolute values, and mathematical function that correlates the BG trends and absolute values.

Some system embodiments may be directed to a fluid delivery system for delivering a recommended bolus dose of therapeutic fluid into the body and include a fluid dispensing unit and, in some embodiments, a remote control unit configured for inputting the one or more first parameters and one or more second parameters into the fluid dispensing unit. The fluid dispensing unit may include, according to some embodiments, at least one processor having instructions operating thereon for assessing and/or storing in memory user-related parameters. The instructions may be configured to receive input related to an initial bolus dose of therapeutic fluid for a user or receive one or more first parameters relating to the user to quantify an initial bolus dose, receive one or more second parameters relating to the user, assess the one or more second parameters, assign a correlating multiplier value to at least one of the one or more second parameters and derive a recommended bolus dose of therapeutic fluid. In some embodiments deriving a recommended bolus dose may include multiplying the initial bolus dose by the multiplier value of at least one of the one or more second parameters. The system may include a display for presenting the recommended bolus dose of therapeutic fluid to the user and a dispensing mechanism for delivering the recommended bolus dose of therapeutic fluid into the body.

Embodiments of the systems may include any of the features described in the present disclosure, including any of the features described above in relation to the methods as well as any one or more of the above and/or following features.

Some embodiments of the present disclosure may be directed to a dispensing unit for delivering a recommended bolus dose of therapeutic fluid to the body. The device may include at least one processor including instructions operating thereon for assessing and storing in memory user-related parameters. The processor, according to some embodiments, may be configured to receive input related to an initial bolus dose of therapeutic fluid for a user or one or more first parameters relating to the user to quantify an initial bolus dose. The processor may receive one or more second parameters relating to the user, assess the one or more second parameters, assign a correlating multiplier value to at least one of the one or more second parameters and derive a recommended bolus dose of therapeutic fluid by multiplying the initial bolus dose by the multiplier value of at least one of the one or more second parameters. The dispensing unit may have a display for presenting the recommended bolus dose of therapeutic fluid to the user and/or a dispensing mechanism for delivering the recommended bolus dose of therapeutic fluid into the body.

Some device embodiments of the present disclosure may be directed to a drug delivery device having a dispensing mechanism, a processor for providing a bolus dose recommendation based on current trend of user physiologic parameters or current physiological conditions, a display for presenting a recommendation of the appropriate insulin bolus dosage and input means to execute the bolus dose recommendation.

In some embodiments, the bolus dose recommendation may be determined in accordance with one or more of the BG trend, physical activity level, emotional stress level, blood ketones level and/or trend, the blood pH level and/or trend, the presence of an illness and/or menstruation or body temperature.

Embodiments of the devices may include any of the features described in the present disclosure, including any of the features described above in relation to the methods, systems and devices, as well as any one or more of the above and/or following features.

Some device embodiments may be directed to an insulin delivery device coupled with a continuous glucose monitor and having a dispensing mechanism, a processor providing a bolus dose recommendation based on the BG trend derived from the continuous glucose measurements. In some embodiments the device may further include a display presenting a recommendation of the appropriate insulin bolus dosage and/or input means to execute the bolus dose recommendation.

Embodiments of the devices may include any of the features described in the present disclosure, including any of the features described above in relation to the methods, systems and devices, as well as any one or more of the above and/or following features.

According to some embodiments, a user and/or caregiver may assign different multiplier values (MVs) and/or absolute values (AVs) to each parameter when initially setting up and/or programming certain device and system embodiments of the present disclosure, e.g., a therapeutic fluid delivery pump. According to some embodiments, multiplier values (MVs) and/or absolute values (AVs) assigned to each parameter may be recommended based on IS values. For example, a user with a high and low IS value may be provided with small and large bolus doses, respectively, in response to changing BG levels.

In some embodiments, systems of the present disclosure may include a remotely-controlled dispensing unit having a reusable part and a disposable part. The disposable part may contain a reservoir, an outlet port and other inexpensive components. The reusable part may contain electronics (e.g., a printed circuit board and/or a processor), driving mechanism and other relatively expensive components. In some embodiments, the dispensing unit may deliver therapeutic fluid to the body, which may be carried out manually by operating one or more switches or buttons located on a dispensing unit.

In some embodiments, a cradle unit may be provided with the dispensing unit. The cradle unit may be a substantially flat sheet that adheres to the skin and allows disconnection and reconnection of the dispensing unit from and to the user's skin at the user's discretion. After attachment of the cradle unit to the skin, a cannula for delivery of fluid therapeutic fluid (e.g., insulin) may be inserted into a subcutaneous portion of the body through a dedicated passageway in the cradle unit. Some embodiments of the dispensing unit may be configured as a patch-like unit for discreet positioning on the body.

DETAILED DESCRIPTION

Figure 1A:
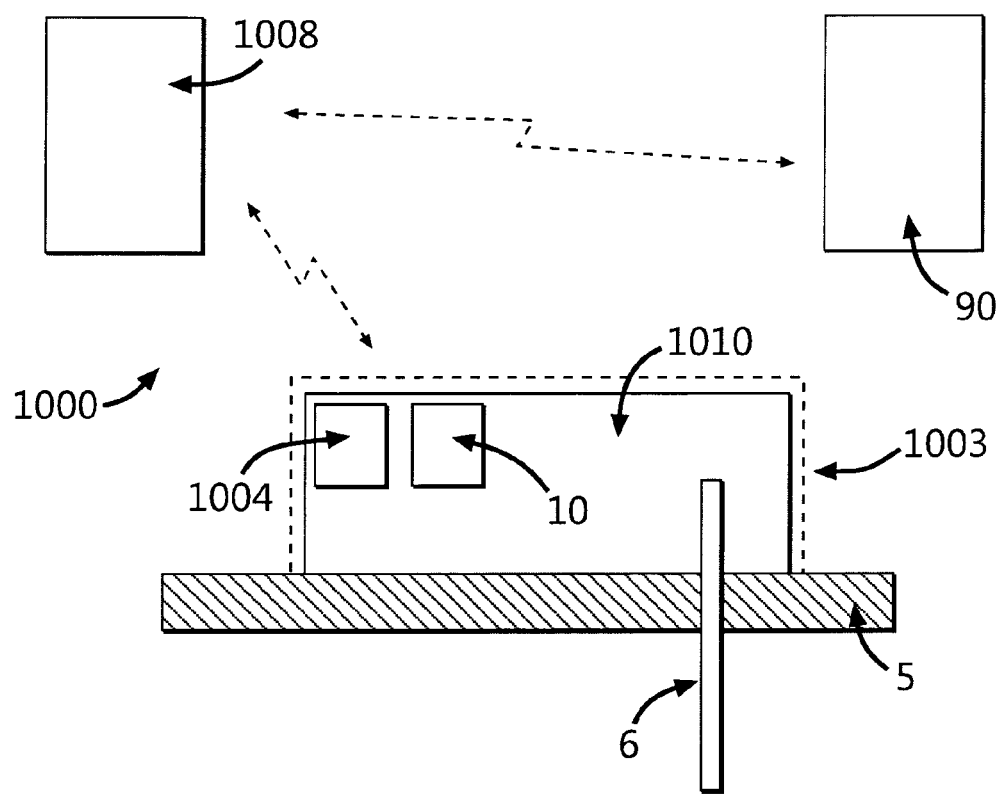
FIGS. 1a-1c illustrate a fluid delivery system including a dispensing unit and a remote control unit according to some embodiments of the present disclosure.

Devices, systems and methods for delivering therapeutic fluid (e.g., insulin) and determining a recommended amount based on one or more user parameters are provided herein. The mechanism or feature for determining a recommended bolus dose based on one or more user parameters (e.g., variables or conditions) may be referred to as the "bolus advisor." To this end, the bolus advisor may be configured to operate within or in conjunction with a fluid dispensing system. In some embodiments, the bolus advisor may be implemented in a fluid dispensing unit and, in particular, in a portable therapeutic fluid infusion pump. The terms "dispensing," "delivery" and "infusion" are used herein interchangeably to refer to the administration or distribution of a substance into the body.

Some embodiments of the present disclosure are directed to a fluid delivery system. The system may include a user interface configured for receiving input from a user (also referred to as "patient"), including without limitation initial bolus dose amounts and/or one or more user parameters, a memory configured to store data, including some or all of a user's input, and a processor or controller (e.g., a CPU or MCU) configured to determine the bolus dose amounts to be delivered. Some embodiments may further include a real time clock ("RTC"). In some embodiments, the system may include a display (e.g., screen) for providing a representation (e.g., visual indication) of one or more parameters, for example, indicating increases or decreases in BG levels using arrows.

In some embodiments, the system may be a remotely-controlled, and may be also securable to the skin (e.g., a patch pump adherable to the skin of the patient). The system may further include a remote control unit. Some embodiments of the system may also include an analyte sensing device (e.g., glucometer, a glucose monitor). In some embodiments, the sensing device may be located in the remote control unit, in a dispensing component of the system, shared in both, or located in another component of the system. In some embodiments, the sensing device may include a CGM. In some embodiments, the CGM may be located in a dispensing component of the system.

Embodiments of the present disclosure may be configured to determine an initial bolus dose (also interchangeably referred to throughout this disclosure as an "original bolus dose") and adjust that amount to a recommended bolus dose. According to some embodiments, determining the original bolus dose may be based on one or more user parameters, including without limitation, one or more of IS, CIR, TBG, TC, RI, glycemic index ("GI"), fat content and CBG. In some embodiments, adjusting the original bolus dose to a recommended bolus dose may be based on user parameters which may include without limitation BG trends (as provided by a CGM or any other suitable means for assessing BG levels), physical activity levels, illness, body temperature, menstruation, emotional stress, blood ketones and blood gases (e.g., $O_2$ saturation). Any one or more of these parameters may be assigned a multiplier value ("MV") that represents the magnitude of that parameter on a relative scale.

Embodiments of the present disclosure may thus be configured to recommend a bolus dose by multiplying the original bolus dose amount by the multiplier values (MVs) of a given number of user parameters.

The MVs may be determined, for example, by matching tables and/or mathematical correlation or calculation. The MVs may be represented as fractions, percentages, or any other mathematical presentation.

In some embodiments, an absolute value ("AV") may be assigned to any one or more of these parameters, which may be added to or subtracted from the original bolus dose to determine a recommended bolus dose. The AV may be determined, for example, by matching tables and/or mathematical correlation or calculation.

By way of example, if a conventional formula for determining a bolus dose is used, as depicted directly below, an initial bolus dose of 10 U may be calculated based on relevant user parameters, as follows:

Parameters:
TC=90 g
CIR=15 g/U
CBG=200 mg/dL
TBG=100 mg/dL
IS=50 mg/dL per unit of insulin
RI=0,
Initial Bolus Dose:

[(TC/CIR)+(CBG−TBG)/IS]−RI=[(90/15)+(200−100)/50]−0=10 U

A recommended bolus dose may then be derived based on one or more additional parameters input into the dispensing unit and/or system by the user by assigning a multiplier value (MV) to each additional parameter to correlate each parameter to a relative magnitude. For example, a physical activity level parameter may be assigned an MV of 0.8 and a BG trend parameter may be assigned an MV of 1.2. Accordingly, the recommended bolus dose may be determined by multiplying the original bolus dose (i.e., 10 U) by these MVs as follows (for example) to get 9.6 U (i.e., the 10 U is adjusted downward by 0.4 U): 10 U*0.8 *1.2=9.6 U. Other mathematical relationships between the MVs may be used.

According to some embodiments the multiplier values (MVs) and/or absolute values (AV), as discussed further herein, may be related to other user-specific parameters, such as a medical condition, blood chemistry or any other clinically-relevant parameter. A user may enter specific parameters (e.g., physical activity level) and, accordingly, the bolus dose may be modified by multiplying the initial bolus dose by the one or more multiplier values (MVs). For example, a physical activity level of a user may be divided into four levels, with each level being represented by a multiplier value (MV) as follows:

Intensive activity (e.g., running): MV=0.5
High activity (e.g., walking): MV=0.8
Sedentary (e.g., sitting): MV=1
Sleep: MV=1.2

According to this example, when the physical activity level is high, the multiplier value (MV) may be less than 1, indicating that a smaller bolus dose is required, and when the physical activity level is low, the multiplier value (MV) may be greater than 1, indicating that a larger is required.

In some embodiments, the bolus advisor may then calculate a recommended a bolus dose by multiplying the MV of the physical activity level by the initial bolus dose.

According to some embodiments, a recommended bolus dose may be calculated using one or more of the above-mentioned parameters and associated MVs. For example, the following equation may be used, in which the influence of all MVs is averaged:

Recommended Bolus Dose=Original Bolus Dose*
$((MV_1+MV_2+ \ldots +MV_n)/n)$, wherein n is the number of parameters included in the calculation. The "Original Bolus Dose" in the formula represents the bolus dose as provided by a known formula, for example. A numerical example is provided below.

"Original Bolus Dose" (using a known, conventional formula): 4 U
Parameter 1 (physical activity level): $MV_1$=0.5
Parameter 2 (BG Trend—glucose going up): $MV_2$=1.3
Parameter 3 (menstruation—present): $MV_3$=1.1

Recommended Bolus Dose=4*((0.5+1.3+1.1)/3)
=3.87 U

In some embodiments, each parameter may influence the recommended bolus dose differently, so that a weighted average of MV may be provided rather than a simple mean.

Figure 1B:
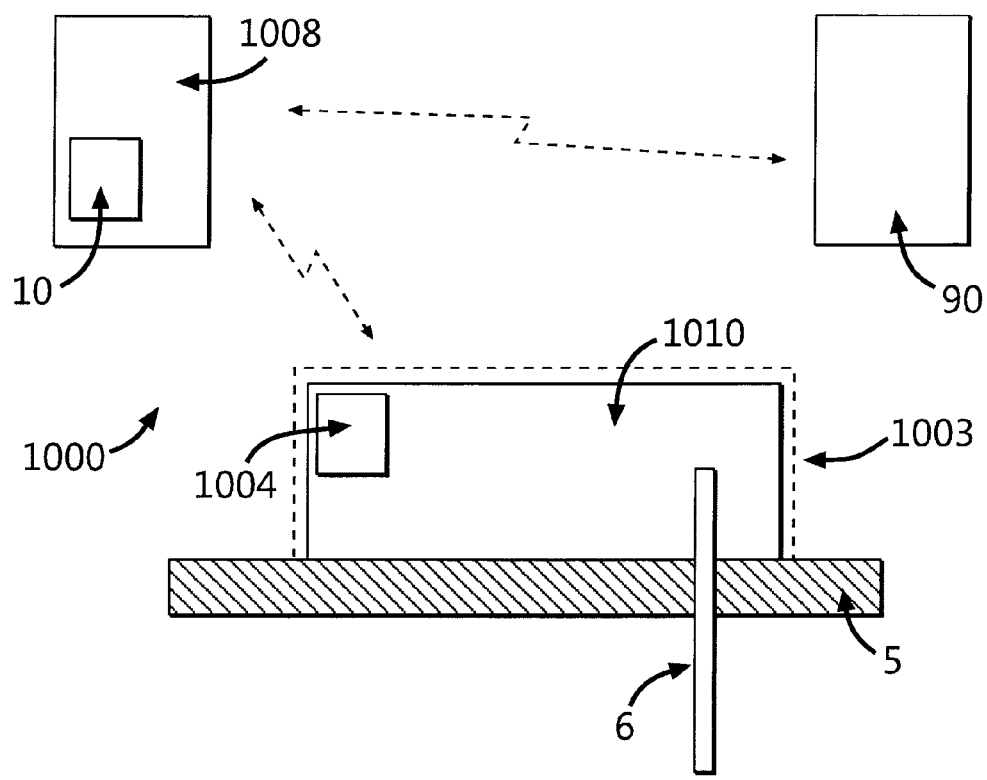
Figure 1C:
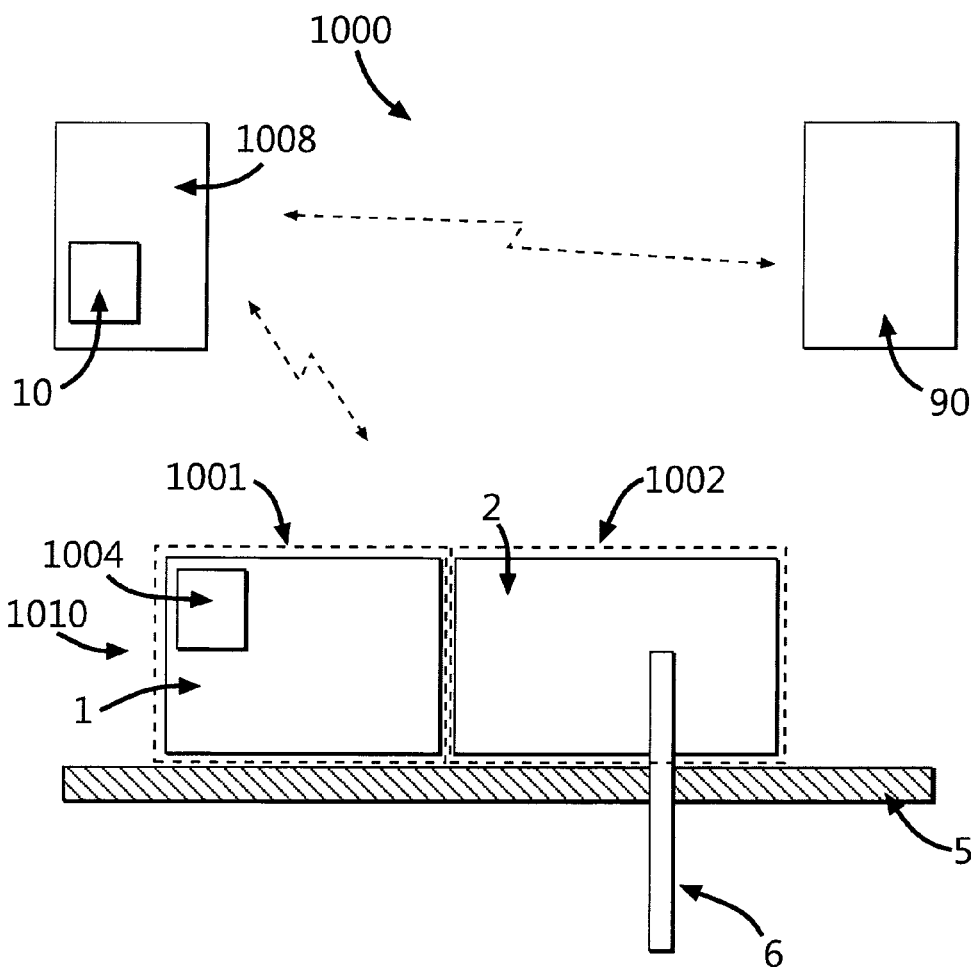

In some embodiments, the MVs may represent the relative change in the original bolus dose corresponding to each parameter. For example, an MV of 1.3 indicates an addition of 30% to the original bolus dose, and an MV of 0.7 indicates a deduction of 30% from the original bolus dose. To calculate a recommended bolus dose based on a plurality of parameters, the relative changes (e.g., the additional 30%) may be summed up, then added to 1 and the result may multiply the original bolus dose. In this example, the sum of relative changes is (−50%)+30%+10%=(−10%) or (−0.5)+0.3+0.1=(−0.1), thus the recommended bolus dose is determined by multiplying the original bolus dose (4 U) by (1+sum of relative changes), i.e., 4*(1+(−0.1))=3.6 U. FIGS. 1a-1c show a fluid delivery system 1000 for dispensing therapeutic fluids (e.g., insulin) into the body of a patient according to some embodiments of the present disclosure. Some embodiments of the system 1000 may include a dispensing unit 1010 having a dispensing mechanism (e.g., syringe with a propelling piston, peristaltic), a remote control unit 1008 and may also include a glucose monitor 90 (e.g., a blood glucose monitor "BGM"). The dispensing unit 1010 may be connected to a cannula 6 that penetrates a patient's skin 5 to deliver therapeutic fluid (e.g., insulin) into the body (e.g., subcutaneous tissue). The dispensing unit 1010 may be a single component having a single housing 1003 (as shown in FIGS. 1*a* and 1*b*) or a two-part component having two housings 1001 and 1002 (as shown in FIG. 1*c*). In some embodiments, housing 1001 (or part 1) maybe reusable and housing 1002 (or part 2) may be disposable. In some embodiments, the reusable part 1 (or reusable housing 1001) may include relatively expensive components, such as electronics, a processor, at least a portion of a driving mechanism, sensors, motors and various other components. Some embodiments of the disposable part 2 (or disposable housing 1002) may include relatively less expensive components, such as a reservoir for containing therapeutic fluid (e.g., insulin), a connecting tube for delivering therapeutic fluid, and a piston and/or plunger assembly for pumping fluid from the reservoir into the body, and the like. Other pumping mechanisms such as peristaltic, piezoelectric, and the like may be used. A power supply (e.g., one or more batteries) for providing power to at least one of the reusable and/or disposable parts of the fluid dispensing unit may be located in the disposable part, the reusable part, or shared therebetween. The power supply may be rechargeable or non-rechargeable. In some embodiments, the disposable part may also be configured with a portion of the driving mechanism, such that the driving mechanism would be shared, under those circumstances, by both parts (the disposable and the reusable).

In some embodiments, flow programming and data acquisition may be accomplished using remote control unit 1008 or directly by one or more operating buttons and/or switches 1004 located on the dispensing unit 1010. Some embodiments of the system 1000 may include at least one processor or controller, at least one memory, at least one input means (e.g., a keypad, keys, mouse, buttons, switches, touch-screen or audio/voice commander), at least one screen or display and at least one notification means. The notification means may include without limitation audible means (e.g., a buzzer) and/or vibrational means (e.g., a vibrator) to notify the user. Each of the foregoing components may reside in the remote control unit 1008, the dispensing unit 1010 or both, or in other components of the system. Embodiments of the remote control unit 1008 may be implemented, for example in one of a Personal Data Assistance ("PDA"), a cellular phone, a watch, a media player (e.g., an iPod), a smartphone (e.g., an iPhone or Android devices), a laptop, an iPad and/or a PC. Example embodiments of system 1000 are disclosed in U.S. Patent Application Publication No. 2007/0106218 to Yodfat et al. and International Publication No. WO 2009/125398 to Yodfat et al., the disclosures of which are incorporated herein by reference in their entireties.

In some embodiments, the system 1000 may include at least one of a BGM, CGM or both. The BGM and/or CGM may be contained within the remote control unit 1008 and/or the dispensing unit 1010, and/or another component of the system. In some embodiments, the BGM and/or CGM may be contained in a separate unit configured to establish one- or two-way communication (e.g., wireless, RF or IR induction) with the dispensing unit 1010 and/or the remote control unit 1008. In some embodiments, the glucose monitor may be shared between a plurality of units/part/components of the system. In some embodiments, a CGM contained within the dispensing unit 1010 may be positioned within the reusable part of the unit 1010, the disposable part of the unit 1010 or both. Some embodiments may include a sensing element (e.g., an electrochemical sensor or one or more electrodes) disposed on the cannula 6. Example embodiments are disclosed in U.S. Patent Application Publication Nos. 2007/0191702 to Yodfat et al. and 2008/0214916 to Yodfat et al., as well as International Publication No. WO 2009/066288 to Yodfat et al., the disclosures of which are incorporated herein by reference in their entireties. In some embodiments, a bolus advisor 10 may be located in the dispensing unit 1010 (see FIG. 1*a*), the remote control unit 1008 (see FIGS. 1*b* and 1*c*) or within both units (1010 and 1008). In some embodiments, the bolus advisor 10 may be implemented in another component of the system, such as a PC.

Figure 2A:
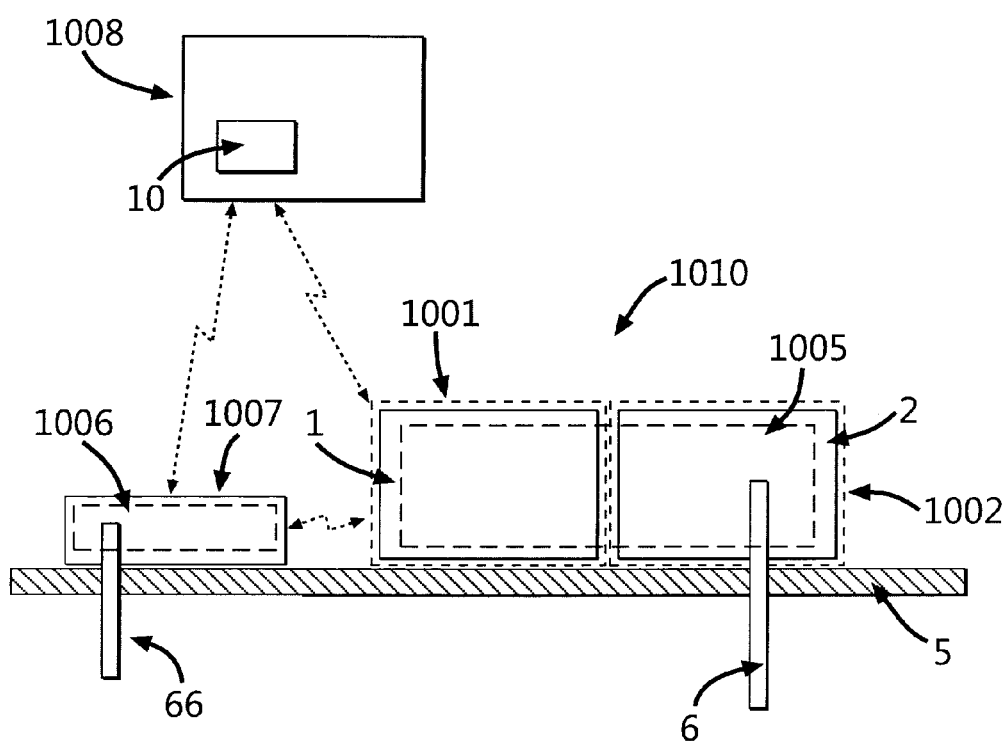
FIGS. 2a-2b illustrate a fluid delivery system including one or more CGMs configured to assess BG Trends according to some embodiments of the present disclosure.
Figure 2B:
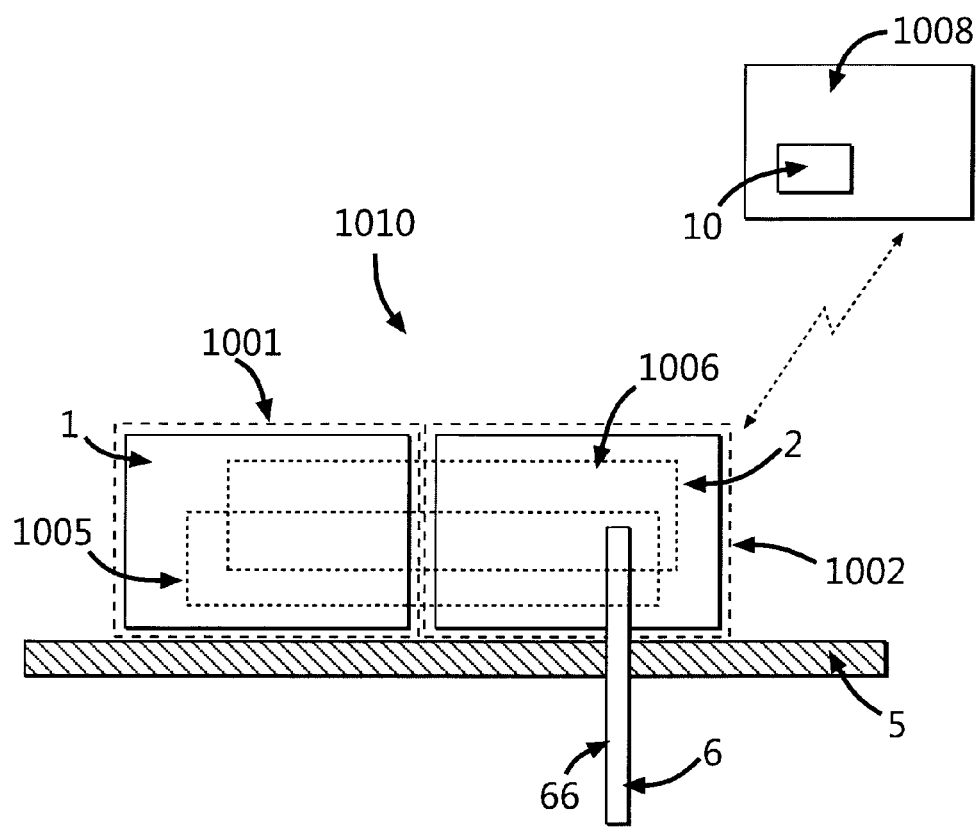

FIGS. 2*a* and 2*b* show a system 1000, according to some embodiments of the present disclosure, having a two-part dispensing unit 1010, a remote control unit 1008 and a CGM unit 1007. In some embodiments, the two-part dispensing unit 1010 may include housings 1001 and 1002. In some embodiments, housing 1001 (or part 1) maybe reusable and a housing 1002 (or part 2) may be disposable. The dispensing unit 1010 may contain a dispensing mechanism 1005 that may be positioned within either or both of housing 1001 and housing 1002. The bolus advisor 10 may be included within the remote control unit 1008 (see FIG. 2*a*), dispensing unit 1010 (see FIG. 1*a*) or both.

FIG. 2*a* specifically shows a system embodiment having a two-part dispensing unit 1010 and a stand-alone CGM unit 1007. The CGM unit 1007, in some embodiments, may have a probe 66 and a sensing mechanism 1006. Embodiments of the sensing mechanism 1006 may include without limitation a processor, a transmitter and a memory. According to some embodiments of the present disclosure, continuous glucose readings obtained by the CGM unit 1007 may be transmitted to the remote control unit 1008 and/or the dispensing unit 1010, as indicated by the arrows shown in FIG. 2*a*.

FIG. 2*b* specifically shows a system embodiment having two-part dispensing unit 1010 that includes a dispensing mechanism 1005 and an onboard CGM unit (not shown). The CGM unit may have a probe 66 and a sensing mechanism 1006. In some embodiments, the dispensing mechanism 1005 may deliver therapeutic fluid (e.g., insulin) through a cannula 6 and the sensing mechanism 1006 may obtain continuous glucose readings using probe 66. According to some embodiments, probe 66 may be located within or on the cannula 6, as described in U.S. Patent Application Publication Nos. 2007/0191702 to Yodfat et al. and 2008/0214916 to Yodfat et al., and International Publication No. WO 2008/078319 to Yodfat et al., the disclosures of which are incorporated herein by reference in their entireties. Yet, in some embodiments, the cannula 6 and probe 66 may be configured apart from one another to allow therapeutic fluid delivery in one location and glucose sensing in another location.

In some embodiments, bolus doses of therapeutic fluid (e.g., insulin) may be recommended by the bolus advisor 10 based on determined BG trends received from the continuous glucose readings obtained from the sensing mechanism 1006. In some embodiments, the BG trends may be computed by a processor based on BG levels received from the CGM. The BG trend may indicate the change and/or the rate of change in BG levels.

In some embodiments, therapeutic fluid (e.g., insulin) may be automatically delivered into the body by the dispensing mechanism 1005 according to continuous BG level readings obtained by the sensing mechanism 1006. In some embodiments, the sensing mechanism 1006 may operate in a closed-loop mode (i.e., automatic feedback with no need for user interaction) or in a semi-closed loop mode (or semi-open loop mode) (i.e., requiring user interaction to confirm instructions). Some embodiments of the present disclosure may be configured to automatically modify basal delivery amounts according to continuous glucose readings obtained by sensing mechanism 1006. In some embodiments, bolus doses may be delivered by way of a user manually inputting (e.g., an open loop mode) the bolus dose based on recommended amounts received from the bolus advisor 10.

Figure 3:
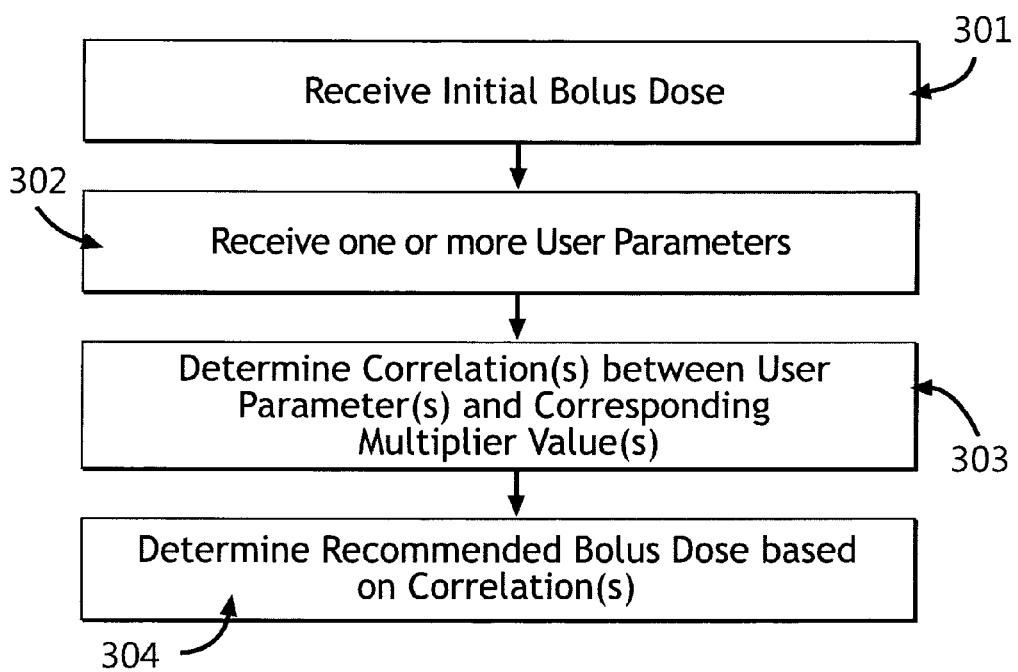
FIG. 3 illustrates a flow diagram for deriving a recommended bolus dose according to some embodiments of the present disclosure.

FIG. 3 is an example of a flow diagram depicting a procedure for deriving a recommended bolus dose using the bolus advisor 10 according to some embodiments of the present disclosure. At step 301, an original bolus dose (e.g., an initial bolus dose) may be provided by a user or a currently-available bolus dose recommendation tool (e.g., a known formula or bolus selector feature) based on a glucose level measurement (e.g., discrete BG level measurement) and/or consumed meal. This bolus dose amount may be entered into the dispensing unit 1010 (see FIGS. 2a and 2b) using onboard switches and/or buttons 1004 and/or via remote control unit 1008. In some embodiments, the original bolus dose may be determined based on one or more parameters including without limitation IS, CIR, TBG, CBG, TC, GI, fat content of the meal, and RI. In some embodiments, the TC may be zero when the patient is not consuming (or intend to consume) food.

At step 302, a user may input, via a user interface for example, one or more additional user parameters (e.g., variables or conditions) into the dispensing unit 1010, according to some embodiments. These parameters may include one or more BG trends (as provided by a CGM, for example), physical activity levels, indicators as to the presence of an illness, body temperature values, emotional stress levels and/or any other suitable parameters relating to the user. These parameters may be programmed into the dispensing unit 1010 (see FIGS. 2a and 2b) using onboard switches and/or buttons 1004 and/or via remote control unit 1008. In some embodiments, the one or more additional user parameters may be transmitted to the dispensing unit 1010. For example, the CGM unit may transmit BG trend(s) to the bolus advisor.

At step 303, each parameter programmed into dispensing unit 1010 may be associated with a multiplier value (MV). The correlation between each specific parameter and corresponding MV may be performed by the bolus advisor 10 using one or more of matching tables, mathematical correlation or calculation, for example. The bolus advisor 10 may operate in conjunction with a processor or controller contained within dispensing unit 1010 or remote control unit 1008 and also memory contained with dispensing unit 1010 or remote control unit 1008.

At step 304, the bolus advisor 10, according to some embodiments, may then determine (e.g., calculate) and output a recommended bolus dose as a function of the different multiplier values (MVs) and the original bolus dose from step 301. In some embodiments, the bolus advisor 10 may provide a notification to the user via a suitable notification means (e.g., a graphic display, beeper, buzzer or vibrator) regarding the recommended bolus dose.

Figure 4:
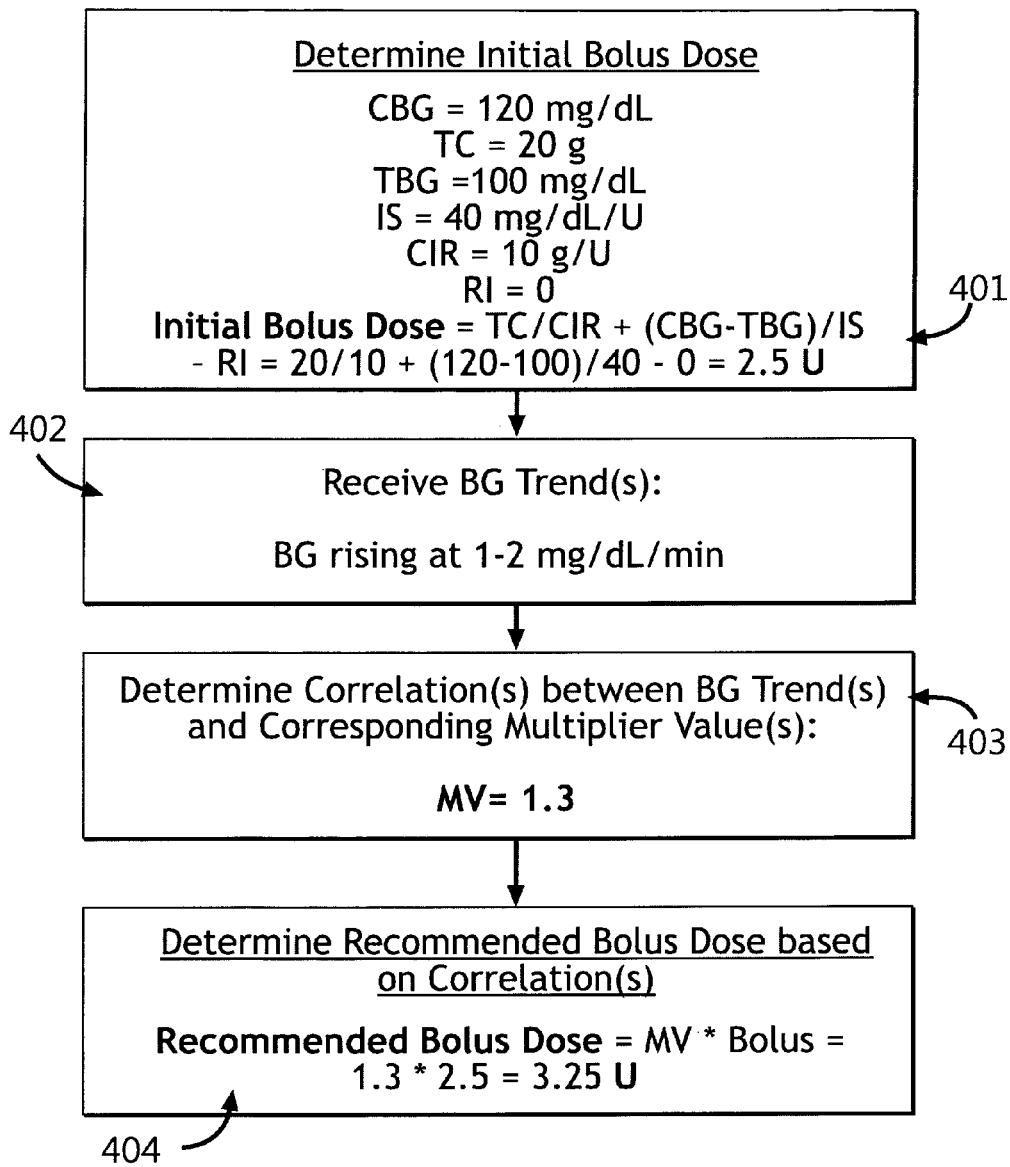
FIG. 4 illustrates a flow diagram for deriving a recommended bolus dose based on a BG Trend, including a numerical example, according to some embodiments of the present disclosure.

FIG. 4 is an example of a flow diagram depicting a procedure, according to some embodiments of the present disclosure, for deriving a recommended bolus dose using the bolus advisor 10. In some embodiments, the recommended bolus dose may depend on a single additional parameter, such as the BG trend of a user, as exemplified in FIG. 4. At step 401, a user's IS, CIR, TBG, CBG, TC and RI values are provided to calculate an initial bolus dose (e.g., original bolus dose) in accordance with a known formula or a bolus selector feature. In some embodiments, one or more of the values may be zero. The formula use in the exemplary procedure in FIG. 4 is shown at step 401. In the given example, an initial bolus dose of 2.5 U is calculated based on the provided user parameters (i.e., IS, CIR, TBG, CBG, TC and RI) and the chosen formula. Other formulas or means for determining a bolus dose may be used.

At step 402, a BG trend parameter is provided by a CGM. In the given example, the BG level is increasing at a rate of 1 to 2 (mg/dL)/min. This rate, according to some embodiments, may be graphically represented on a display (e.g., of the dispensing unit 1010 and/or remote control unit 1008), by an arrow pointing in the 2 o'clock direction. In some embodiments, the devices and/or systems of the present disclosure may be coupled to a CGM and have a memory configured to store BG level measurements and/or BG trends, and a processor configured to assess the continuous blood glucose concentration measurements and identify trends (e.g., increases and/or decreases) in BG levels. According to some embodiments, BG trends may be represented via vectors (e.g., 5 vectors) and graphically depicted as follows on a display:

↑=glucose rising quickly: >2 (mg/dL)/min=
↗=glucose going up: >1 (mg/dL)/min=
→=fairly stable glucose: >−1 (mg/dL)/min<1 (mg/dL)/min
↘=glucose going down: <−1 to −2 (mg/dL)/min
↓=glucose falling quickly: <−2 (mg/dL)/min At step 403, the BG trend parameter may be correlated with a multiplier value (MV) of 1.3, which may correlate with the given BG trend of blood glucose concentration increasing at a rate graphically depicted by an arrow pointing in the 2 o'clock direction. In some embodiments, each BG trend vector (or range of BG trend vectors) may be represented by a certain multiplier value (MV) that correlates the magnitude of a particular user parameter to a relative scale. For example:

↑=glucose rising quickly: MV=1.6
↗=glucose going up: MV=1.3
→=fairly stable glucose: MV=1
↘=glucose going down: MV=0.7
↓=glucose falling quickly: MV=0.4

According to some embodiments, and by way of example only, when a BG trend parameter is down, the multiplier value (MV) will be less than about 1, as shown directly above. Conversely, in some embodiments, if a BG trend parameter is up, the multiplier value (MV) will be larger than about 1. If a BG trend parameter is fairly constant (i.e., no change in blood glucose concentration), the MV would be about 1.

At step 404, a recommended bolus dose is calculated and provided by the bolus advisor 10. The recommended bolus dose may equal the multiplier value (MV) multiplied against the initial bolus dose of 2.5 U from step 401, i.e. a bolus dose of 3.25 U (1.3*2.5). Embodiments of the present disclosure may be configured to use the bolus advisor to derive recommended bolus doses by multiplying an original bolus dose (e.g., initial bolus dose) amount by the multiplier values (MV) of one or more BG trend parameters. The original bolus dose may be determined by the user by direct estimation of TC, by a known formula for calculating a bolus dose or by a bolus selector feature (for example). Exemplary formulas that may be used are described in U.S. Patent Application Publication No. 2008/0234663 to Yodfat et al. and International Publication No. WO 2009/133558 to Yodfat et al., or U.S. Pat. No. 6,936,029 to Mann et al, the disclosures of which are incorporated herein by reference in their entireties.

In some embodiments, the recommended bolus dose may be smaller than the original bolus dose if the BG trend indicates that the blood glucose level is going down or falling. In further embodiments, the recommended bolus dose may be higher than the original bolus dose if the BG trend indicates that the blood glucose level is going up or rising. In some embodiments, the recommended bolus dose may be substantially equal to the original bolus dose if the BG trend indicates a substantially constant level of the blood glucose level.

A numerical example correlating a multiplier value (MV) to a quickly-rising glucose trend of >2(mg/dL)/min is provided below:

Parameters:
  IS=50
  CIR=15
  TBG=100
  TC=90 g (e.g., pepperoni pizza)
  CBG=200 (mg/dL)
Parameters with Assigned Correlated Values:
  BG Trend: >2 (mg/dL)/min (MV=1.6)
Options for Determining the Recommended Bolus Dose:
  implementing User Estimation of Bolus Dose=about 10 U
    (e.g., user knows that pepperoni pizza is approximately 10 units of insulin)

Recommended Bolus Dose=Estimation*MV=10 U*1.6=16 U implementing a formula:

[(TC/CIR)+(CBG−TBG)/IS]*MV=[((90/15)+(200−100))/50]*1.6=16 U

Embodiments of the present disclosure may be directed to determining a recommended bolus dose based on CBG and BG trend(s). For example, if the CBG is normal (e.g., substantially equals the TBG or is within a normal range) and a BG trend is increasing, the bolus advisor 10 may determine a recommended bolus dose according to the rising slope.

In some embodiments the bolus advisor 10 may determine the amount of fluid to be delivered via a bolus dose (e.g., a correction bolus or meal bolus) according to the CBG, BG trend or any other relevant parameters, including without limitation, IS, CIR, TBG, TC, GI, fat content of the meal, RI, physical activity level, emotional stress level, blood ketones level and/or trend, blood pH level and/or trend, presence of an illness and/or menstruation or body temperature. For example, for a certain meal the bolus advisor 10 may determine (and/or recommend) a larger bolus dose when the BG trend is increasing compared to when the BG trend is constant. Conversely, for a certain meal, the bolus advisor 10 may determine (and/or recommend) a smaller bolus dose when the BG trend is decreasing compared to when the BG trend is constant.

In some embodiments, the bolus advisor 10 may adjust the bolus timing (i.e., the point in time at which bolus dose delivery is initiated) and/or duration (i.e., the distribution over time of the bolus dose) based on one or more of the following parameters: IS, CIR, TBG, CBG, BG trend, TC, GI, fat content of the meal, RI, physical activity level, emotional stress level, blood ketones level and/or trend, blood pH level and/or trend, presence of an illness and/or menstruation or body temperature. In some embodiments, the bolus advisor 10 may control the dispensing unit 1010 to prolong the delivery time duration of the bolus dose, shorten the delivery time duration, delay the delivery or distribute the delivery dose unequally across the delivery time duration. For example, the bolus advisor 10 may determine a bolus dose according to a known formula or a bolus selector feature and determine the delivery timing and/or duration based, at least in part, on the BG trend.

In some embodiments, the bolus advisor 10 may determine (and/or recommend) to delay the delivery of a meal bolus dose if the CBG is low and the BG trend indicates that the BG level is rising. In some embodiments, the bolus advisor 10 may determine (and/or recommend) to shorten the delivery duration of a bolus dose (e.g., a correction bolus or a meal bolus) if the CBG is high and the BG trend indicates that the BG level is increasing. In some embodiments, the bolus advisor 10 may determine (and/or recommend) to distribute a meal bolus dose unequally if the CBG is normal and the BG trend is increasing, to first counteract both the rising BG level and the meal TC and later to counteract only the TC (depending on the contents of the meal, for example).

Figure 5:
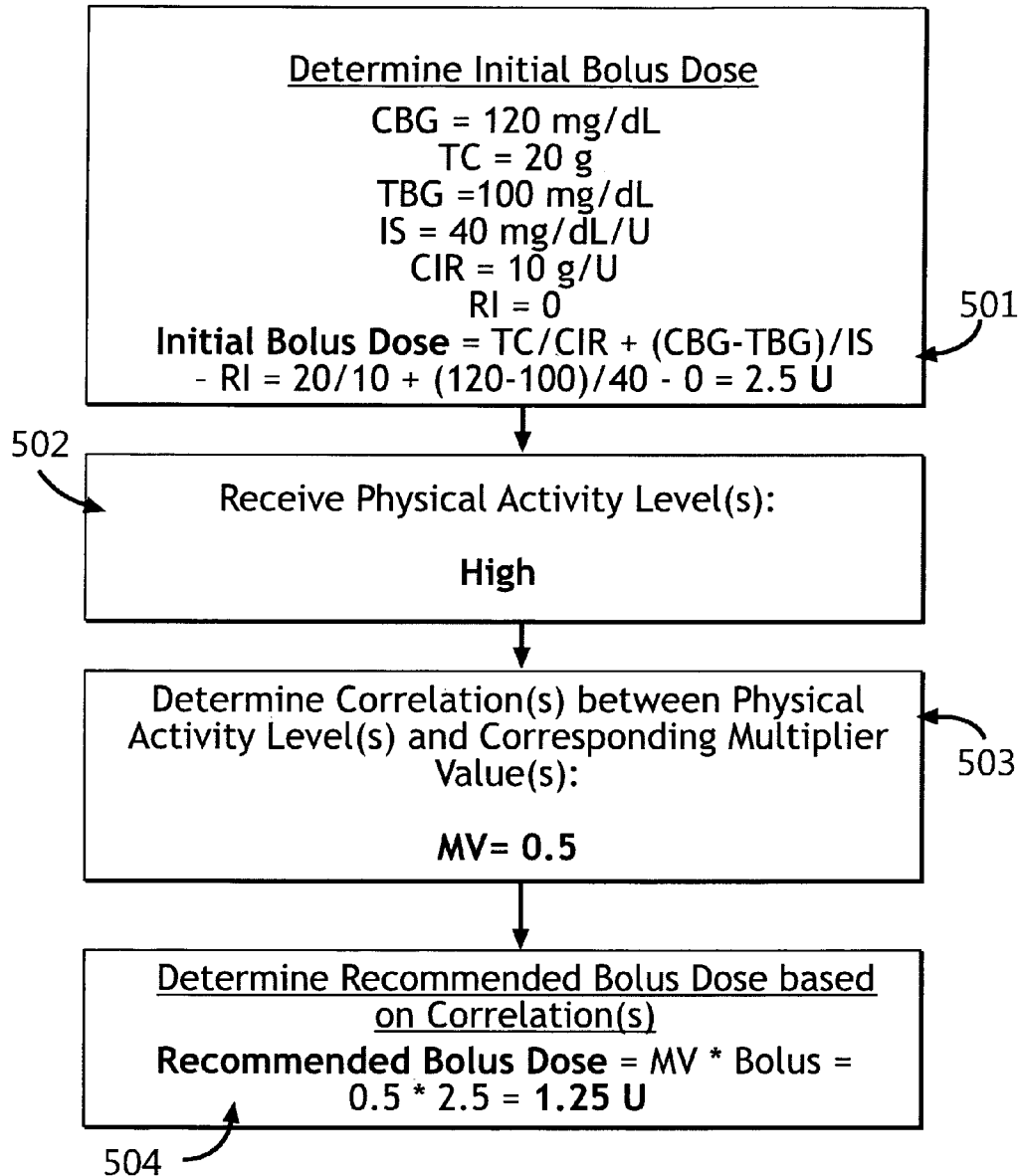
FIG. 5 illustrates a flow diagram for deriving a recommended bolus dose based on physical activity level, including a numerical example, according to some embodiments of the present disclosure.

FIG. 5 is an example of a flow diagram depicting a procedure, according to some embodiments of the present disclosure, for deriving a recommended bolus dose using the bolus advisor 10. In some embodiments, the recommended bolus dose may depend on a single additional parameter, such as a user's physical activity level, as shown in FIG. 5. At step 501, a user's IS, CIR, TBG, CBG, TC and RI values are provided to calculate an initial bolus dose in accordance with a known formula or a bolus selector feature. The formula used in the exemplary procedure in FIG. 5 is shown at step 501. In the given example, an initial bolus dose of 2.5 U is calculated based on the provided user parameters (i.e., IS, CIR, TBG, CBG, TC and RI) and the chosen formula.

At step 502 a physical activity level parameter is inputted by the user, e.g., a "High" physical activity level designation. At step 503, this physical activity level parameter may be correlated by the bolus advisor with a multiplier value (MV). For example a value of 0.5 may correlate to the given physical activity level designation of "High." Conversely, if the user had entered "Low" for this parameter, the bolus advisor may have assigned an MV of 0.8, for example, to the parameter. At step 504, a recommended bolus dose is calculated and output by the bolus advisor. The recommended bolus dose may equal the multiplier value (MV) multiplied against the initial bolus dose from step 501, i.e. a bolus dose of 1.25 U (0.5*2.5).

In some embodiments, user parameters (e.g., BG trends or physical activity levels) may be assigned an absolute value ("AV") of a bolus dose that may be added or subtracted from the initial bolus dose. In some embodiments, the AV may be a constant value. In some embodiments, the AV may be correlated to and/or dependent upon other parameters, such as for example CBG, TBG, and BG trend. In further embodiments, the AV and/or MV may be also dependent on time (i.e., vary with time) according to a predetermined pattern or mathematical function, or correlated to at least one parameter. According to some embodiments, one or more parameters may be assigned an absolute value (AV) of an initial bolus dose and one or more parameters may be assigned a multiplier value (MV). By way of example, a BG trend parameter may be assigned an absolute value (AV) and added to the initial bolus dose and a physical activity level parameter may be assigned a multiplier value (MV) and multiplied against the remainder of the formula as shown below to derive a recommended bolus dose:

Parameters:
  TC=90 g
  CIR=15 g/U
  CBG=200 mg/dL

TBG=100 mg/dL
IS=50 mg/dL per unit of insulin
RI=0.
Parameters with Assigned Correlated Values:
BG trend: rising at 1-2 mg/dL/min→add=1.2 U
Physical activity level: MV=0.8
Recommended Bolus Dose:

$$[(90/15)+(200-100)/50+1.2]*0.8=7.36 \text{ U}$$

In some embodiments, as discussed above with respect to FIG. 4, the BG trend may be divided into multiple vectors, wherein each BG trend vector may be represented by a certain multiplier value (MV). Furthermore, according to some embodiments, each BG trend vector (or range of BG Trend vectors) may be represented by a certain absolute value (AV) of bolus dose that may also (or instead) be added or subtracted from the initial bolus dose, for example:

↑=glucose rising quickly: AV=2 U
↗=glucose going up: AV=1 U
→=fairly stable glucose: AV=0 U
↘=glucose going down: AV=−1 U
↓=glucose falling quickly: AV=−2 U In some embodiments, when a BG trend parameter is down the absolute value of the AV parameter may be subtracted from the original bolus dose (as less insulin is required). In some embodiments, if a BG trend parameter is up, the AV may be added (as more insulin is required). In some embodiments, if a BG trend is constant (i.e., no change in blood glucose concentration), the AV will be 0.

Embodiments of the present disclosure may recommend a bolus dose by adding and/or subtracting the AV of a BG trend to and/or from, respectively, the initial bolus dose amount provided by a user's estimation of TC or by a known formula.

A recommended bolus dose may then be derived based on one or more additional parameters input into the dispensing unit 1010 and/or system 1000 by the user by assigning an absolute value (AV) to each additional parameter to correlate each parameter to a relative magnitude. Accordingly, the recommended bolus dose may be determined by adding or subtracting these AV's from the original bolus dose.

According to some embodiments, a recommended bolus dose may be calculated using one or more of the above-mentioned parameters and associated AVs. For example, the following equation may be used:

Recommended Bolus Dose=Original Bolus Dose+/−
  $((AV_1+AV_2+ \ldots +AV_n)/n)$, wherein n is the number of parameters included in the calculation. The "Original Bolus Dose" in the formula represents the bolus dose as provided by a known formula, for example.

In some embodiments, each parameter may influence the recommended bolus dose differently, so that a weighted average of AV may be provided rather than a simple mean.

Various embodiments of the subject matter described herein can be realized in digital electronic circuitry, integrated circuitry, specially designed ASICs (application specific integrated circuits), computer hardware, firmware, software, and/or combinations thereof. These various embodiments may include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein can be implemented on a computer having a display device (e.g., a CRT (cathode ray tube), LCD (liquid crystal display) monitor, or other display device) for displaying information to the user and a keyboard and a pointing device (e.g., a mouse or a trackball) by which the user may provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The subject matter described herein can be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system can be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Some embodiments of the present disclosure preferably implement the bolus advisor 10 via software operated on a processor contained in a remote control device of an insulin dispensing system and/or a processor contained in an insulin dispensing device being part of an insulin dispensing system.

Any and all references to publications or other documents, including but not limited to, patents, patent applications, articles, Web pages and/or books disclosed in the present application are incorporated herein by reference in their entireties.

Although a few variations have been disclosed in detailed disclosure above, this has been done by way of example for purposes of illustration only and is not intended to be limiting with respect to the scope of the appended claims. Accordingly, a person having ordinary skill in the art will understand and recognize that other modifications are possible. For example, the logic flow depicted in the accompanying figures and described herein does not require the particular order shown, or a sequential order, to achieve desirable results. Other embodiments, implementations, aspects, advantages and modifications may be considered within the scope of the appended claims, as well as any other potential claims supported by this disclosure.

What is claimed is:

1. A method for determining a recommended bolus dose of therapeutic fluid to be delivered to the body of a user, the method comprising:
receiving by a processor a current blood glucose level (CBG) of the user;
receiving by the processor a BG trend including a direction and/or rate of change of blood glucose level (BG) of the user;
receiving by the processor one or more additional parameters relating to the user;
determining by the processor an initial bolus dose of the therapeutic fluid for the user before delivery to the body of the user based on the CBG, the BG trend and the one or more additional parameters relating to the user;
determining by the processor a recommended bolus dose to be delivered to the body of the user based on the initial bolus dose being multiplied by one or more multiplier values, wherein the one or more multiplier values represent a magnitude on a relative scale of an associated one of the BG trend and the one or more additional parameters, such that delivering the recommended bolus dose to the user compensates for a change in a BG level of the user, and wherein the recommended bolus is determined by the processor after determining the initial bolus dose and before delivery of any one of the initial bolus dose and the recommended bolus dose; and
notifying, by the processor, the user of the recommended bolus dose.

2. The method of claim 1, wherein the one or more additional parameters relating to the user are selected from a group consisting of insulin sensitivity (IS), carbohydrate-to-insulin ratio (CIR), target blood glucose level (TBG), an amount of carbohydrate to be consumed (TC), and residual insulin (RI).

3. The method of claim 1, wherein the one or more additional parameters relating to the user are selected from a group consisting of: glycemic index (GI), fat content of the meal, and fiber content of the meal.

4. The method of claim 1, wherein the CBG is measured via a continuous glucose monitor (CGM).

5. The method of claim 1, wherein the BG trend is received from a continuous glucose monitor (CGM).

6. The method of claim 1, wherein at least one of the one or more additional parameters relating to the user, the CBG and the BG trend is received via a user interface.

7. The method of claim 1, further comprising retrieving, from a memory, the one or more multiplier values correlating to the BG trend.

8. The method of claim 1, wherein determining the recommended bolus dose includes adding or subtracting one or more absolute values to or from the initial bolus dose.

9. The method of claim 8, further comprising retrieving, from a memory, the one or more absolute values corresponding to the BG trend.

10. The method of claim 8, wherein:
the one or more absolute values are added when the BG trend is increasing;
the one or more the absolute values are subtracted when the BG trend is decreasing; and
the one or more absolute values equals 0 when the BG level is constant.

11. The method of claim 8, wherein the one or more absolute values are determined based on a mathematical function that correlates the BG trend with the one or more absolute values.

12. The method of claim 1, wherein the one or more multiplier values correlate to the BG trend, and wherein the one or more multiplier values are greater than 1 when the BG trend is increasing; the one or more multiplier values are less than 1 when the BG trend is decreasing; and the one or more multiplier values equal 1 when the BG level is constant.

13. The method of claim 1, wherein the one or more multiplier values are determined based on a mathematical function that correlates the BG trend with the one or more multiplier values.

14. The method of claim 1, wherein the notifying is via a display.

15. The method of claim 1, further comprising delivering the therapeutic fluid according to the recommended bolus dose.

16. The method of claim 1, wherein the one or more additional parameters relating to the user has a first group of parameters comprised of one or more of insulin sensitivity (IS), carbohydrate-to-insulin ratio (CIR), target blood glucose level (TBG), an amount of carbohydrate to be consumed (TC), residual insulin (RI), a received user input via a user interface, glycemic index (GI), and content of the meal, and a second group of parameters comprised of physical activity level, emotional stress level, blood ketones level and/or trend, blood pH level and/or trend, presence of an illness and/or menstruation, and body temperature, and wherein the initial bolus dose is based on the one or more of the additional parameters being selected from the first group of parameters and the CBG, and the one or more multiplier values correlate with at least one of the one or more additional parameters being selected from the second group of parameters and the BG trend.

17. The method of claim 1, wherein determining the recommended bolus dose comprises:
averaging a plurality of multiplier values of the one or more multiplier values, wherein at least one of the one or multiplier values correlates to the BG trend; and
determining the recommended bolus dose includes multiplying the initial bolus dose with the average of the plurality of multiplier values.

18. The method of claim 1, further comprising adjusting a timing and/or duration associated with the recommended bolus dose based on at least the BG trend.

19. The method of claim 1, wherein:
the recommended bolus dose is less than the initial bolus dose if the BG trend is decreasing;
the recommend bolus dose is greater than the initial bolus dose if the BG trend is increasing; and
the recommended bolus dose equals the initial bolus dose if the BG level of the user is constant.

20. The method of claim 1, wherein the therapeutic fluid comprises insulin.

21. The method of claim 1, further comprising receiving by the processor, from a user interface, the one or more multiplier values correlating to the one or more additional parameters.

22. A method for determining a recommended bolus dose of therapeutic fluid to be delivered to the body of a user, the method comprising:

receiving by a processor a current blood glucose level (CBG) of the user;

receiving by the processor a BG trend including a direction and/or rate of change of blood glucose level (BG) of the user;

receiving by the processor one or more additional parameters relating to the user;

determining by the processor an initial bolus dose of the therapeutic fluid for the user before delivery to the body of the user based on the CBG, the BG trend and the one or more additional parameters relating to the user;

determining by the processor a recommended bolus dose to be delivered to the body of the user based on the initial bolus dose being multiplied by one or more multiplier values, wherein the one or more multiplier values represent a magnitude on a relative scale of an associated one of the BG trend and the one or more additional parameters, such that delivering the recommended bolus dose to the user compensates for a change in a BG level of the user, and wherein the recommended bolus is determined by the processor after determining the initial bolus dose and before delivery of any one of the initial bolus dose and the recommended bolus dose; and notifying, by the processor, the user of the recommended bolus dose, wherein the one or more additional parameters relating to the user has a first group of parameters is comprised of insulin sensitivity (IS), carbohydrate-to-insulin ratio (CIR), target blood glucose level (TBG), an amount of carbohydrate to be consumed (TC), residual insulin (RI), a received user input via a user interface, glycemic index (GI), fat content of the meal, and fiber content of the meal, and a second group of parameters comprised of physical activity level, emotional stress level, blood ketones level and/or trend, blood pH level and/or trend, presence of an illness and/or menstruation and body temperature, and wherein the initial bolus dose is based on the one or more of the additional parameters being selected from the first group of parameters and the CBG, and the one or more multiplier values correlate with at least one of the one or more additional parameters being selected from the second group of parameters and the BG trend.

* * * * *

UNITED STATES PATENT AND TRADEMARK OFFICE
CERTIFICATE OF CORRECTION

PATENT NO. : 9,919,105 B2
APPLICATION NO. : 13/496716
DATED : March 20, 2018
INVENTOR(S) : Ofer Yodfat, Gali Shapira and Iddo M. Gescheit Page 1 of 1

It is certified that error appears in the above-identified patent and that said Letters Patent is hereby corrected as shown below:

Column 21, Line 66, Claim 10:
"the one or more the absolute values are subtracted when"
Should read:
--the one or more absolute values are subtracted when--; and Column 22, Line 45, Claim 17:
"or multiplier values correlates to the BG trend; and"
Should read:
--or more multiplier values correlates to the BG trend; and--; and Column 22, Line 55, Claim 19:
"the recommend bolus dose is greater than the initial bolus"
Should read:
--the recommended bolus dose is greater than the initial bolus--; and Column 24, Line 6, Claim 22:
"is comprised of insulin sensitivity (IS), carbohydrate-"
Should read:
--comprised of insulin sensitivity (IS), carbohydrate- --.

Signed and Sealed this
Eighteenth Day of June, 2019

Andrei Iancu
*Director of the United States Patent and Trademark Office*